(12) United States Patent
Langowski et al.

(10) Patent No.: US 8,158,019 B2
(45) Date of Patent: Apr. 17, 2012

(54) ORGANIC OXYGEN SCAVENGER/INDICATOR

(75) Inventors: Horst-Christian Langowski, Zolling (DE); Thomas Wanner, Schrobenhausen (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 222 days.

(21) Appl. No.: 12/093,341

(22) PCT Filed: Nov. 17, 2006

(86) PCT No.: PCT/EP2006/011076
§ 371 (c)(1),
(2), (4) Date: Jul. 16, 2008

(87) PCT Pub. No.: WO2007/059901
PCT Pub. Date: May 31, 2007

(65) Prior Publication Data
US 2008/0272336 A1 Nov. 6, 2008

(30) Foreign Application Priority Data
Nov. 22, 2005 (DE) .................. 10 2005 055 633

(51) Int. Cl.
| C09K 3/00 | (2006.01) |
| B01D 53/14 | (2006.01) |
| C01B 13/00 | (2006.01) |
| B01J 20/22 | (2006.01) |
| B65D 81/24 | (2006.01) |
| B65D 81/26 | (2006.01) |
| B65D 81/28 | (2006.01) |
| A23B 7/14 | (2006.01) |
| A23B 7/153 | (2006.01) |
| A23B 7/154 | (2006.01) |

(52) U.S. Cl. ........ 252/184; 423/219; 502/401; 426/133; 426/268

(58) Field of Classification Search .................. 252/184; 502/401; 426/133, 268; 423/219
See application file for complete search history.

(56) References Cited

U.S. PATENT DOCUMENTS
| 2,685,516 A | 8/1954 | Wilson |
| 3,134,673 A | 5/1964 | Ganguin |
(Continued)

FOREIGN PATENT DOCUMENTS
DE 102004009870 B3 10/2005
(Continued)

OTHER PUBLICATIONS

Marianiova et al., "Electrical conductivity measurements of hyaluronic acid and collagen." Colloid Polym. Sci., 271, 143-147 (1993).*

(Continued)

*Primary Examiner* — Stuart Hendrickson
*Assistant Examiner* — Daniel Berns
(74) *Attorney, Agent, or Firm* — Timothy X. Gibson; Gibson & Dernier LLP

(57) ABSTRACT

The invention relates to an oxygen scavenger/indicator which contains at least one substance with combined scavenger and indicator function for oxygen, which can absorb oxygen under the effect of moisture in basic conditions, and also to at least one basically reacting compound. The indicator effect is effected by a change in at least one physical property of the substance with combined scavenger and indicator function for oxygen, the change being triggered by the effect of moisture.

33 Claims, 2 Drawing Sheets

U.S. PATENT DOCUMENTS

| | | | |
|---|---|---|---|
| 4,230,595 A * | 10/1980 | Yamaji et al. | 252/188.28 |
| 4,289,645 A | 9/1981 | Muccitelli | |
| 4,626,411 A | 12/1986 | Nemes et al. | |
| 4,971,918 A | 11/1990 | Bouse et al. | |
| 5,180,518 A * | 1/1993 | Sugihara et al. | 252/188.28 |
| 5,667,863 A * | 9/1997 | Cullen et al. | 428/68 |
| 2004/0048011 A1 * | 3/2004 | Ekman et al. | 428/34.1 |
| 2004/0086749 A1 * | 5/2004 | Kennedy et al. | 428/690 |
| 2005/0205840 A1 * | 9/2005 | Farneth et al. | 252/188.28 |
| 2006/0145091 A1 * | 7/2006 | Patel | 250/474.1 |

FOREIGN PATENT DOCUMENTS

| | | |
|---|---|---|
| WO | 02099416 A1 | 12/2002 |
| WO | WO 2004/077097 * | 9/2004 |
| WO | 2005085836 A1 | 9/2005 |

OTHER PUBLICATIONS

International Search Report for International Application PCT/EP2006/011076 (Feb. 26, 2007).

Written Opinion for International Application PCT/EP2006/011076 (Feb. 26, 2007).

* cited by examiner

ORGANIC OXYGEN SCAVENGER/INDICATOR

FIELD OF THE INVENTION

The invention relates to an oxygen scavenger/indicator which contains at least one substance with combined scavenger and indicator function for oxygen, which can absorb oxygen under the effect of moisture in basic conditions, and also to at least one basically reacting compound. The indicator effect is effected by a change in at least one physical property of the substance with combined scavenger and indicator function for oxygen, the change being triggered by the effect of moisture.

BACKGROUND $O_2$ scavengers are materials which can sorb oxygen. There should be understood here by sorption all the known sorption possibilities, e.g. adsorption, absorption, chemical adsorption and physical adsorption. The systems established at present according to the state of the art can be qualified here primarily according to the $O_2$ scavenger substrate and according to the initialisation mechanism thereof. The following groups are hereby differentiated:
- inorganic $O_2$ scavengers, e.g. iron-based or sulphide-based systems
- low molecular organic $O_2$ scavengers, e.g. ascorbate-based systems
- high molecular organic $O_2$ scavengers, e.g. polyolefin-based or polyamide-based systems $O_2$ scavengers are thereby initialised either by UV radiation or by moisture. This means that the $O_2$ scavenger function is present only after exposure to UV radiation or water, i.e. air moisture.

Indicator systems in general can be subdivided into time-temperature indicator (TTI), gas/leakage indicator and freshness indicator systems.

A TTI integrates the time-temperature history of a product and hence provides direct evidence about the storage conditions thereof. The indicator effect is effected by a chemical reaction or by counter-diffusion of two colourants.

Gas-leakage indicators detect the gas concentration of $O_2$, $CO_2$ or $H_2O$ in the packaging space. Hence they provide direct evidence about the quality of the product. The indicator effect is caused by a chemical reaction with the reactands $O_2$, $CO_2$ or $H_2O$.

Freshness indicators detect the metabolic products of microorganisms and hence provide direct evidence about the quality of the product. The indicator effect is caused by a chemical reaction of the metabolic products.

It is common to all these indicator systems that the indicator effect is reproduced by a visible colour change.

Hence there is a large number of $O_2$ scavenger systems in the state of the art but only a decreasingly low number of gas-leakage indicator systems.

In particular for the packager and also for the seller of products (foodstuffs), the information about how the headroom atmosphere in the packaging behaves would however be important. Furthermore, with establishment of active packaging with $O_2$ scavengers, the knowledge about the residual consumption capacity of the packaging (e.g. at the time of packaging) is of the greatest interest.

SUMMARY OF THE INVENTION

Combined $O_2$ scavenger/indicator systems are at present not known in the state of the art. In the case of these, the $O_2$ scavenger operates independently of the $O_2$ indicator, i.e. the $O_2$ indicator signals merely that a certain $O_2$ concentration is exceeded.

Starting herefrom, it was the object of the present invention to provide an $O_2$ scavenger/indicator system which can signal visually or measurably that a certain $O_2$ concentration timespan is exceeded and also that an absorbed oxygen quantity of the $O_2$ scavenger is exceeded.

This object is achieved by the oxygen scavenger/indicator having at least one substance with combined scavenger and indicator function for oxygen, which sorbs oxygen under the effect of moisture in basic conditions, at least one component of the indicator changing at least one of its physical properties, and also at least one basically reacting compound. The object may be achieved by the composite system containing at least one carrier layer and at least one oxygen scavenger/indicator. Further advantages are revealed herein.

DETAILED DESCRIPTION OF THE INVENTION

Figure 1:
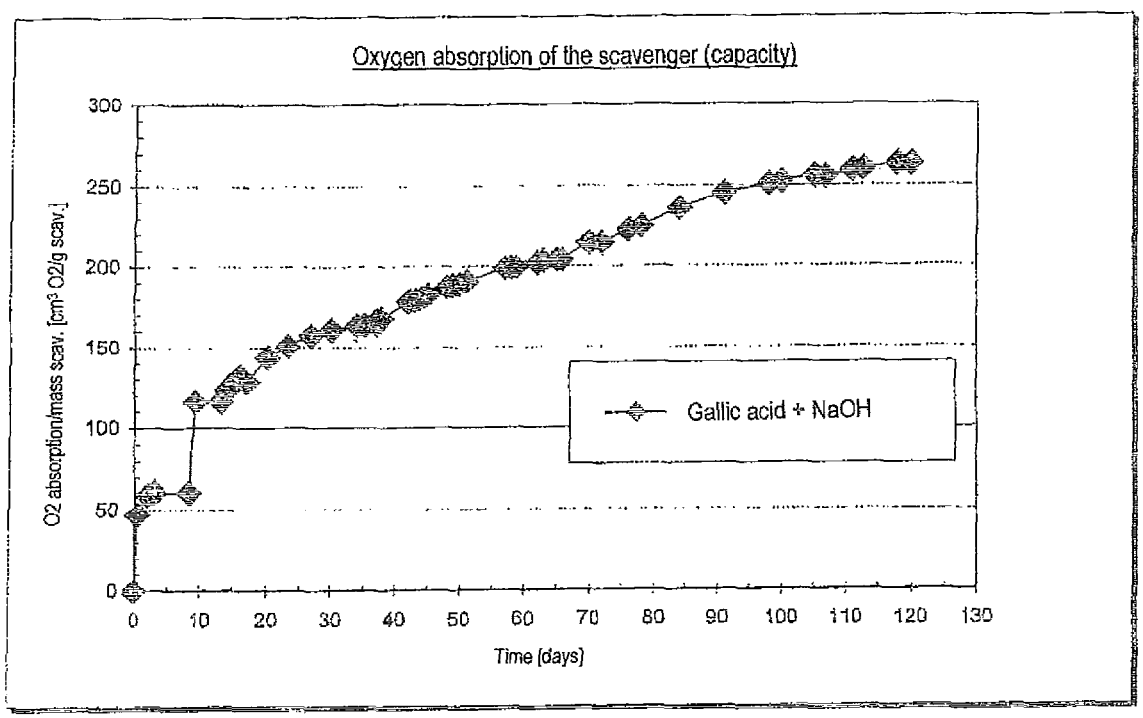
FIG. 1 shows the oxygen absorption over time of the $O_2$ scavenger/indicator based on gallic acid and NaOH, the system being present in powder form.

According to the invention, an oxygen scavenger/indicator is provided, which contains at least one substance with combined scavenger and indicator function for oxygen, which can sorb oxygen under the effect of moisture in basic conditions, the at least one substance with combined scavenger and indicator function for oxygen changing at least one of its physical properties because of the sorption of the oxygen. Furthermore, the indicator contains a basically reacting compound.

The substance with combined scavenger and indicator function for oxygen can hereby serve both alone as oxygen scavenger/indicator or as combined oxygen scavenger and oxygen scavenger/indicator. This essentially depends upon the weight proportions of the substance with combined scavenger and indicator function for oxygen and upon the further components contained in the oxygen scavenger/indicator.

The added basically reacting compound has the effect that a basic medium is produced, in which then the substance with combined scavenger and indicator function for oxygen can sorb the oxygen. In the dry state, the result is however no oxygen sorption because of the lack of a basic medium. Preferably water, i.e. the air moisture found in the environment, serves as trigger for the reaction with oxygen. As a result of air moisture, the basically reacting compound dissolves with the production of a basic medium. By exceeding a certain relative moisture, the result is hence initialisation of the system, the relative air moisture of the initialisation being able to be determined by the choice of basically reacting compound and/or of the electrolyte. A typical value in the use of NaCl as electrolyte for initiation of the system is $\geq 75\%$ relative air moisture.

The substance with combined scavenger and indicator function for oxygen can change at least one of its physical parameters under oxygen exposure in a basic medium. With respect to the physical properties mentioned here, there are no restrictions as long as they represent a visual or metrologically evaluatable change in the substance with combined scavenger and indicator function for oxygen.

There should be mentioned hereby as physical properties in particular the magnetism, electrical conductivity and electromagnetic absorption of the substance with combined scavenger and indicator function for oxygen. The electromagnetic absorption thereby relates in particular to the microwave, IR, visible or UV range so that the changes in electromagnetic absorption in this wavelength range can be undertaken by corresponding detection methods known from the state of the art.

A first variant according to the invention provides that the substance with combined scavenger and indicator function for oxygen has magnetic properties or is magnetisable. The thereby occurring change in permeability or magnetic remanence can then be detected e.g. by a sensor. A magnetometer is used here for the magnetic remanence whilst the change in permeability can be detected by means of an inductivity measurement.

A further preferred variant provides that the substance with combined scavenger and indicator function for oxygen has electrically conductive properties and increases or reduces the electrically conductive properties by the exposure to oxygen and the therewith associated sorption of the oxygen. Such a change in electrical conductivity can then be detected with the help of a sensor. Coupling of the current is thereby effected by an inductive or capacitive route. The detection during the inductive coupling can preferably be effected by means of eddy current measuring technology. In the case of capacitive coupling, detection can be effected preferably according to the condenser principle.

A further preferred variant with respect to the physical properties relates to the electromagnetic absorption of the substance with combined scavenger and indicator function for oxygen. As a result of the sorption of oxygen, the result hereby is a changed electromagnetic absorption of the substance with combined scavenger and indicator function for oxygen, which in turn can be determined by means of a corresponding detector. Preferably, the UV or IR range is used here for the detection, photometers or IR measuring devices acting here as detectors. In the visible range just as in the microwave range, detection is however possible in the same way.

The oxygen scavenger/indicators according to the invention are based on materials which combine both the $O_2$ scavenger and the $O_2$ indicator function in themselves. Hence the $O_2$ scavenger and the $O_2$ indicator has the same reaction kinetics.

For the invented combined system this implies the further advantage that correlation of the absorbed oxygen quantity of the $O_2$ scavenger with the colour change in the $O_2$ indicator is independent of the temperature.

A system with one material for the $O_2$ scavenger function and with a further material for the $O_2$ indicator function has, in contrast hereto, two reaction kinetics and hence two different temperature dependencies. This means that the correlation of the residual capacity of the $O_2$ scavenger with the colour change in the $O_2$ indicator is temperature-dependent.

Preferably, the substance with combined scavenger and indicator function for oxygen is selected from the group comprising hydroquinone, resorcinol, benzcatechin, salicylic acid, pyrogallol, gallic acid and also the salts and derivatives thereof. Likewise, it is preferred to select polyhydroxycyclohexene, polyhydroxybenzoic acid and also the salts and derivatives thereof.

Preferably the compound which reacts basically with water is selected from the group comprising alkali and alkaline earth metal halogenides, metallic and non-metallic sulphates and phosphates and non-metallic halogenides.

The at least one basically reacting compound is preferably selected from the group of hydroxides, carbonates, sulphides, thiosulphates, oxides, phosphates, polyphosphates of alkali or alkaline earth metals. Likewise, alkali or alkaline earth metal salts of organic acids are preferred. However it is also possible to use any other compounds which react basically with water. Particularly preferred, the oxygen scavenger/indicator contains magnesium hydroxide or sodium thiosulphate as basically reacting compound.

In a further preferred variant, the oxygen scavenger/indicator can contain in addition at least one electrolyte as further additive. The electrolyte is thereby preferably selected from the group of metal halogenides. There are hereby preferred as metals, lithium, sodium, potassium, magnesium, calcium and barium whereas there are used preferably as halogenides, chlorine, bromine, iodine and fluorine. The particularly preferred halogenide hereby is chloride.

However, any other electrolytes known from the state of the art can also be used here which assist the electron transfer of the redox reaction. There may be mentioned here by way of example metallic and non-metallic sulphates and phosphates but also non-metallic halogenides, such as ammonium chloride.

These electrolytes can be present both in liquid and in solid form.

A further preferred variant provides that the oxygen scavenger/indicator contains a polymer- and/or gel electrolyte. There can be used as polymer electrolytes, in particular polymers in combination with salts, such as e.g. polyethylene oxide (PEO) with $LiPF_6$, polypropylene oxide (PPO) with $LiCF_3SO_3$ or polyester oxide with $LiClO_4$ and possibly $TiO_2$. As gel electrolytes, there are used particularly preferably systems comprising polyether, polycarbonate and $LiBF_4$, systems comprising polyacrylonitrile (PAN), polycarbonate (PC), electrochromic polymers and $LiClO_4$ and systems comprising polyvinylchloride (PVC), dioctyladipate (DOA) and $LiN(SO_2CF_3)_2$.

A preferred embodiment of the oxygen scavenger/indicator according to the invention is composed of 75 to 99% by weight of the at least one substance with combined scavenger- and indicator function for oxygen, and 1 to 25% by weight of the at least one compound which reacts basically with water. The data relate to the total weight of the oxygen scavenger/indicator.

Another preferred embodiment of the oxygen scavenger/indicator according to the invention comprises up to 75 to 98.5% by weight of the at least one oxygen sorbent, up to 1 to 15% by weight of the at least one basically reacting compound and up to 0.5 to 10% by weight of the at least one electrolyte.

The oxygen scavenger/indicator according to the invention has the particular feature that the weight ratio of the substance with combined scavenger and indicator function for oxygen to the basically reacting compound and possibly, if present, to the electrolyte can be adjusted such that the oxygen scavenger/indicator changes at least one of its physical properties at a defined time which indicates the residual capacity of the substance with combined scavenger and indicator function for oxygen. Included herein is in particular a colour change point.

A further variant according to the invention provides that the weight ratio of the substance with combined scavenger and indicator function for oxygen to the basically reacting compound and possibly to the electrolyte is adjusted such that the oxygen scavenger/indicator changes at least one of its physical properties at a defined point which indicates that a specific oxygen concentration is exceeded. There is included herein again a colour change point.

A third variant provides that the weight ratio of the substance with combined scavenger and indicator function for oxygen to the at least one basically reacting compound and possibly to the at least one electrolyte is adjusted such that the oxygen scavenger/indicator has a change in its physical properties at a defined time which indicates that a specific oxygen concentration timespan is exceeded. As a preferred physical property there applies here also electromagnetic absorption, i.e. the change in colour of the sorbent. By means of the colour change point, a defined residual capacity of the substance with combined scavenger and indicator function for oxygen is intended to be signalled visually or with the help of a measurement.

All three previously mentioned variants according to the invention can of course also be combined with each other.

It is preferred in addition that at least one of the components of the oxygen scavenger/indicator is contained in encapsulated form. There is included herein in particular that the oxygen scavenger/indicator contains water in encapsulated form. Water capsules of this type can then be destroyed by mechanical stress, as a result of which the water contained in the capsule is released and serves as carrier for the oxygen scavenger/indicator.

Fundamentally, the oxygen scavenger/indicator can be present in two variants, i.e. as non-visible and visible variant. The visible variant thereby enables visual perception and evaluation, which generally is adequate with respect to qualitative evaluations. The non-visible variant is based in turn on the change in other physical properties which—as described previously—are evaluated with corresponding measuring instruments and thus can also provide in addition quantitative results. In particular for the packager and the seller of products, e.g. foodstuffs, the information about how the headroom atmosphere in the packaging behaves is also important. Furthermore, with establishment of active packagings with $O_2$ scavengers, knowledge about the residual consumption capacity of the packaging, e.g. at the time of packaging, is of the greatest interest. These requirements can be achieved outstandingly with the described indicator systems according to the invention.

According to the invention, a composite system is also provided, which contains at least one carrier layer and at least one oxygen scavenger/indicator, as described previously.

Preferably, the at least one oxygen scavenger/indicator is thereby enclosed between the at least one carrier layer and the at least one further layer in the manner of a sandwich. The at least one oxygen scavenger/indicator can thereby be disposed for example in solid, disperse or dissolved form at points between the at least one carrier layer and the at least one further layer. It is also possible that the at least one oxygen scavenger/indicator is disposed in solid, disperse or dissolved form in a planar manner between the at least one carrier layer and the at least one further layer, for example in the form of a film.

The at least one oxygen scavenger/indicator can be embedded in a polymer layer, e.g. comprising polyethylene. It is also possible that the at least one oxygen scavenger/indicator is embedded in an adhesive backing layer, a paint layer or printed ink layer.

The at least one further layer can be modified by foaming and/or stretching. In this way, it is possible to influence the oxygen permeability of the composite system subsequently.

Preferably, the at least one substance with combined scavenger and indicator function for oxygen is present in solid, disperse or dissolved form.

The described composite systems are outstandingly suitable as packaging films for any packaging item, in particular foodstuffs, and also as an individual film within an electrical or electronic appliance.

The fields of application thereby relate to the foodstuffs industry, pharmaceutical products and appliances, the electronics industry, the chemical industry but also cultural and military fields.

Various variants of the subject according to the invention are intended to be represented with reference to the subsequent examples, without restricting said subject to the embodiments shown here.

EXAMPLE 1

Oxygen Consuming/Indicating Sample Mixture

Gallic Acid+NaOH

A powder system based on gallic acid+NaOH binds oxygen. In this system, the beginning of the oxygen sorption is indicated to the user by means of a colour change from white to dark red. The scavenger/indicator is thereby activated by moisture. The system changes the colour according to an absorbed quantity of oxygen of approx. 10 $cm^3/g$.

FIG. 1 shows the oxygen absorption over time of the $O_2$ scavenger/indicator based on gallic acid and NaOH, the system being present in powder form.

EXAMPLE 2

Oxygen Consuming/Indicating Packaging Material

PET/$SiO_x$/KK (Gallic Acid, CaO, NaCl)/PA

Figure 2:
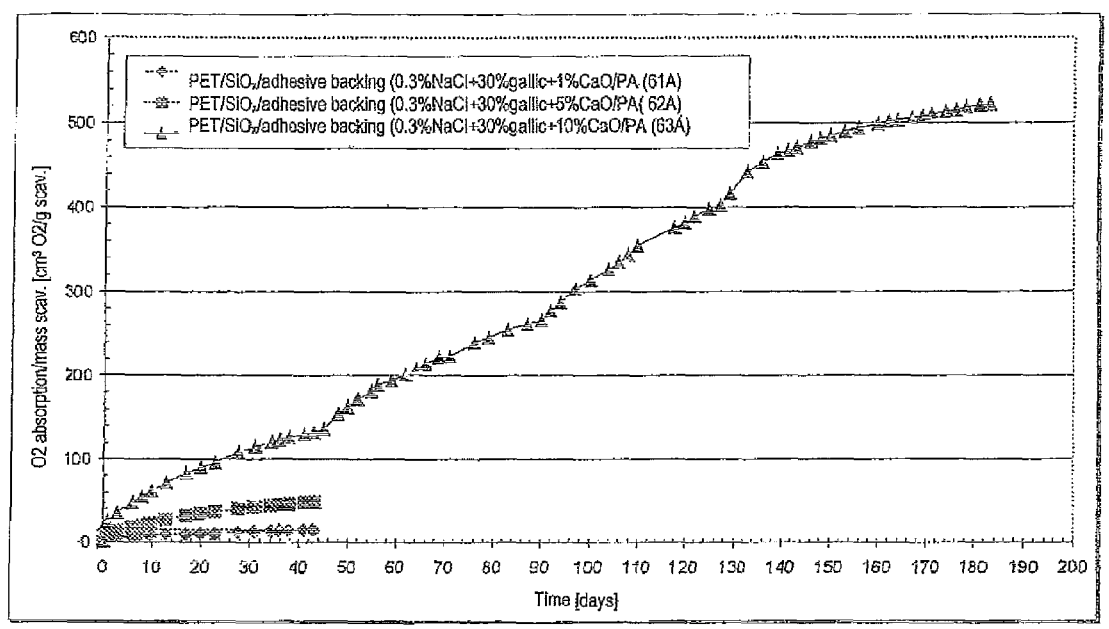
FIG. 2, represents a characterisation of the system comprising gallic acid and CaO, incorporated in an adhesive backing.

In FIG. 2, the characterisation of the system comprising gallic acid and CaO is represented, incorporated in as adhesive backing. The multilayer system produced has the construction of polyethylene terephthalate (PET/$SiO_x$/adhesive backing/polyamide (PA). It advises the user by means of a colour change from transparent to dark purple to the fact that the $O_2$ scavenger is active. The functions are activated by the presence of moisture. The reaction thereby requires moisture and a basic medium, this basic medium being achieved by the reaction of water with calcium oxide to form calcium hydroxide.

What is claimed is:

1. An oxygen scavenger/indicator comprising at least one substance with combined scavenger and indicator function for oxygen, which sorbs oxygen under the effect of moisture in basic conditions, at least one component of the indicator changing at least one of its physical properties, and also at least one basically reacting compound wherein the oxygen scavenger/indicator contains at least one electrolyte as further additive wherein the at least one electrolyte is a polymer electrolyte with salts, wherein the at least one substance with combined scavenger and indicator function for oxygen is an aromatic compound, wherein at least one of the components is present in encapsulated form.

2. The oxygen scavenger/indicator according to claim 1 wherein the at least one substance with combined scavenger and indicator function for oxygen is selected from the group consisting of gallic acid, propyl gallate, and the salts and derivatives thereof.

3. An oxygen scavenger/indicator according to claim 1, wherein magnetism, electrical conductivity and/or electromagnetic absorption of the substance with combined scavenger and indicator function for oxygen changes during the sorption.

4. An oxygen scavenger/indicator according to claim 1, wherein the electromagnetic absorption of the substance with combined scavenger and indicator function for oxygen changes during the sorption and the electromagnetic absorption relates to the microwave, IR, visible or UV range.

5. An oxygen scavenger/indicator according to claim 1 wherein the change in at least one physical property is a colour change.

6. An oxygen scavenger/indicator according to claim 1 wherein at least one compound which reacts basically with water is contained.

7. An oxygen scavenger/indicator according to claim 6 wherein the at least one compound which reacts basically with water is selected from the group consisting of hydroxides, carbonates, sulphites, thiosulphates, oxides, phosphates, polyphosphates of the alkali and alkaline earth metals and alkali and alkaline earth metal salts of organic acids.

8. An oxygen scavenger/indicator according to claim 6, wherein the at least one compound which reacts basically with water is magnesium hydroxide, sodium thiosulphate and/or calcium oxide.

9. An oxygen scavenger/indicator according to claim 1, further comprising an electrolyte selected from the group consisting of alkali and alkaline earth metal halogenides, metallic and non-metallic sulphates and phosphates and non-metallic halogenides.

10. An oxygen scavenger/indicator according to claim 9, wherein the metals are selected from the group consisting of lithium, sodium, potassium, magnesium, calcium and barium and the halogenides are selected from the group consisting of chlorine, bromine, iodine and fluorine.

11. An oxygen scavenger/indicator according to claim 1 wherein the at least one electrolyte is a gel electrolyte.

12. An oxygen scavenger/indicator according to claim 1 wherein the weight ratio of the substance with combined scavenger and indicator function for oxygen to the basically reacting compound and electrolyte is adjusted such that the oxygen scavenger/indicator has a change in at least one physical property at a defined point which indicates the residual capacity of the substance with combined scavenger and indicator function for oxygen.

13. An oxygen scavenger/indicator according to claim 12, wherein the weight ratio of the substance with combined scavenger and indicator function for oxygen to the basically reacting compound, and electrolyte, is adjusted such that the oxygen scavenger/indicator has a colour change point which indicates the residual capacity of the substance with combined scavenger and indicator function for oxygen.

14. An oxygen scavenger/indicator according to claim 1 wherein the weight ratio of the substance with combined scavenger and indicator function for oxygen to the basically reacting compound and electrolyte is adjusted such that the oxygen scavenger/indicator has a change in at least one physical property at a defined point which indicates that a specific oxygen concentration is exceeded.

15. An oxygen scavenger/indicator according to claim 14, wherein the weight ratio of the substance with combined scavenger and indicator function for oxygen to the basically reacting compound and electrolyte is adjusted such that the oxygen scavenger/indicator has a colour change point which indicates that a specific oxygen concentration is exceeded.

16. An oxygen scavenger/indicator according to claim 1 wherein the weight ratio of substance with combined scavenger and indicator function for oxygen to the basically reacting compound and electrolyte is adjusted such that the oxygen scavenger/indicator has a change in at least one physical property at a defined point which indicates that a specific oxygen concentration timespan is exceeded.

17. An oxygen scavenger/indicator according to claim 16, wherein the weight ratio of the substance with combined scavenger and indicator function for oxygen to the basically reacting compound and electrolyte is adjusted such that the oxygen scavenger/indicator has a colour change point which indicates that a specific oxygen concentration timespan is exceeded.

18. An oxygen scavenger/indicator according to claim 1 wherein the oxygen scavenger/indicator is visible.

19. A composite system containing at least one carrier layer and at least one oxygen scavenger/indicator comprising at least one substance with combined scavenger and indicator function for oxygen, which sorbs oxygen under the effect of moisture in basic conditions, at least one component of the indicator changing at least one of its physical properties, and also at least one basically reacting compound wherein the oxygen scavenger/indicator contains at least one electrolyte as further additive wherein the at least one electrolyte is a polymer electrolyte with salts, wherein the at least one substance with combined scavenger and indicator function for oxygen is an aromatic compound, wherein the at least one oxygen scavenger/indicator is enclosed between the at least one carrier layer which represents a barrier layer for oxygen and at least one further layer at least partially permeable for oxygen in the manner of a sandwich.

20. A composite system according to claim 19 wherein the at least one further layer is modified by foaming and/or stretching.

21. A composite system according to claim 19 wherein the at least one oxygen scavenger/indicator is disposed in solid, disperse or dissolved form at points between the at least one carrier layer and the at least one further layer.

22. A composite system according to claim 19 wherein the at least one oxygen scavenger/indicator is disposed in solid, disperse or dissolved form in a planar manner between the at least one carrier layer and the at least one further layer.

23. A composite system according to claim 19 wherein the at least one oxygen scavenger/indicator is embedded in a polymer layer.

24. A composite system according to claim 19 wherein the at least one oxygen scavenger/indicator is embedded in an adhesive backing layer, in a paint layer or in a printed ink layer.

25. A composite system according to claim 19 wherein the layer which contains at least one oxygen scavenger/indicator, and/or the at least one further layer is modified by the addition of polar or non-polar additives.

26. A composite system according to claim 19 in the form of a packaging film or partially applied individual film.

27. The composite system according to claim 19 wherein the at least one substance with combined scavenger and indicator function for oxygen is selected from the group consisting of gallic acid, propyl gallate, and the salts and derivatives thereof.

28. An oxygen scavenger/indicator comprising at least one substance with combined scavenger and indicator function for oxygen, which sorbs oxygen under the effect of moisture in basic conditions, at least one component of the indicator changing at least one of its physical properties, and also at least one basically reacting compound wherein the oxygen scavenger/indicator contains at least one electrolyte as further additive wherein the at least one electrolyte is a polymer electrolyte with salts, wherein the at least one substance with combined scavenger and indicator function for oxygen is an aromatic compound wherein the oxygen scavenger/indicator comprises up to 75 to 98.5% by weight of the at least one substance with combined scavenger and indicator function for oxygen, up to 1 to 15% by weight of the at least one basically reacting compound and the remainder being the at least one electrolyte.

29. The oxygen scavenger/indicator according to claim 28 wherein the at least one substance with combined scavenger and indicator function for oxygen is selected from the group consisting of gallic acid, propyl gallate, and the salts and derivatives thereof.

30. An oxygen scavenger/indicator comprising at least one substance with combined scavenger and indicator function for oxygen, which sorbs oxygen under the effect of moisture in basic conditions, at least one component of the indicator changing at least one of its physical properties, and also at least one basically reacting compound wherein the oxygen scavenger/indicator contains at least one electrolyte as further additive wherein the at least one electrolyte is a polymer electrolyte with salts, wherein the at least one substance with combined scavenger and indicator function for oxygen is an aromatic compound, wherein the oxygen scavenger/indicator is not visible.

31. The oxygen scavenger/indicator according to claim 30 wherein the at least one substance with combined scavenger and indicator function for oxygen is selected from the group consisting of gallic acid, propyl gallate, and the salts and derivatives thereof.

32. A composite system containing at least one carrier layer and at least one oxygen scavenger/indicator comprising at least one substance with combined scavenger and indicator function for oxygen, which sorbs oxygen under the effect of moisture in basic conditions, at least one component of the indicator changing at least one of its physical properties, and also at least one basically reacting compound wherein the oxygen scavenger/indicator contains at least one electrolyte as further additive wherein the at least one electrolyte is a polymer electrolyte with salts, wherein the at least one substance with combined scavenger and indicator function for oxygen is an aromatic compound, wherein the at least one oxygen scavenger/indicator is enclosed between the at least one carrier layer and at least one further layer in the manner of a sandwich, wherein the at least one further layer is modified by foaming and/or stretching.

33. A composite system containing at least one carrier layer and at least one oxygen scavenger/indicator comprising at least one substance with combined scavenger and indicator function for oxygen, which sorbs oxygen under the effect of moisture in basic conditions, at least one component of the indicator changing at least one of its physical properties, and also at least one basically reacting compound wherein the oxygen scavenger/indicator contains at least one electrolyte as further additive wherein the at least one electrolyte is a polymer electrolyte with salts, wherein the at least one substance with combined scavenger and indicator function for oxygen is an aromatic compound, and wherein the at least one oxygen scavenger/indicator is embedded in an adhesive backing layer, in a paint layer or in a printed ink layer.

* * * * *